(12) United States Patent
Kandil et al.

(10) Patent No.: US 6,764,682 B1
(45) Date of Patent: Jul. 20, 2004

(54) ADJUVANT COMPOSITIONS CONTAINING MORE THAN ONE ADJUVANT

(75) Inventors: Ali Kandil, Willowdale (CA); Olive A. James, Toronto (CA); Michel H. Klein, Willowdale (CA); Pele Chong, Richmond Hill (CA)

(73) Assignee: Aventis Pasteur Limited, Toronto (CA)

( * ) Notice: Subject to any disclaimer, the term of this patent is extended or adjusted under 35 U.S.C. 154(b) by 1013 days.

(21) Appl. No.: 08/261,194

(22) Filed: Jun. 16, 1994

(51) Int. Cl.$^7$ ............................................. A61K 39/38
(52) U.S. Cl. .............................. 424/184.1; 424/279.1; 424/682; 424/690; 424/602; 424/208.1; 424/278.1
(58) Field of Search .......................... 424/208.1, 278.1, 424/279.1, 184.1, 682, 690, 602, 641, 693, 698

(56) References Cited

U.S. PATENT DOCUMENTS

| | | | |
|---|---|---|---|
| 4,057,685 A | * 11/1977 | McIntire | 536/55.1 |
| 4,096,245 A | * 6/1978 | Homma et al. | 424/260.1 |
| 4,258,029 A | 3/1981 | Moloney et al. | 424/88 |
| 4,596,792 A | 6/1986 | Vyas | 514/21 |
| 4,599,230 A | 7/1986 | Milich et al. | 424/89 |
| 4,599,231 A | 7/1986 | Milich et al. | 424/89 |
| 4,601,903 A | 7/1986 | Frasch | 424/92 |
| 4,737,488 A | * 4/1988 | Lockhoff et al. | 514/22 |
| 4,762,710 A | * 8/1988 | Sekura | 424/92 |
| 4,855,283 A | * 8/1989 | Lockhoff et al. | 424/278.1 |
| 4,891,425 A | * 1/1990 | Lockhoff et al. | 536/29.1 |
| 4,997,915 A | 3/1991 | Tan et al. | 530/396 |
| 5,070,190 A | * 12/1991 | Lockhoff et al. | 536/22 |
| 5,149,650 A | * 9/1992 | Wertz et al. | 435/243 |

FOREIGN PATENT DOCUMENTS

| | | |
|---|---|---|
| WO | WO 91/00104 | 1/1991 |
| WO | WO 91/13909 | 9/1991 |

OTHER PUBLICATIONS

Alving (1991) J. Immun. Methods 140:1–13.*
Lockhoff (1991) Angew.Chem.In.Ed.Engl. 30:1611–1620.*
Gupta et al (1993) Vaccine 11:293–306.*
Richards et al (1988) Inf. Imm. 56:682–686.*
Deres et al (1989) Nature 342:561–564.*
Wiesmüller et al (1989) Vaccine 7:29–33.*
Nixon–George et al (1990) J. Immunology 144:4798–4802.*
Durette et al. Carbohydrate Research Vol 108, 1982, p 139–147.*
Gupta et al. Vaccine 11(3), 1993, p 293–306.*
Richards et al. Inf and Immunity 56(3), Mar 88, p 682–686.*
Masihi et al. Int J Immunopharmacol 8(3), 1986, p 339–345.*
Stunkel et al. Prog Leukocyte Biol 9 (Cell. Basis Immune Modulation), 1989, p 575–579.*
Penney et al. J Biol Standardization 14(4), 1986, p 345–349.*
Wiesmueller et al. Vaccine 7(1), 1989, p29–33.*
Ramasamy et al. J Natn Sci Coun Sri Lanka 21(1), 1993 p 125–140.*
Vanlandschoot et al., Vaccine vol. 11 issue 12, pp. 1185–1187 "Recombinant secreted haemagglutin protects mice against a lethal challenge of influenza virus", 1993.*
Nixon–George et al (1990), J. Immunology 144: 4798–4802.
Wiesmuller, 1989, Vaccine 8: 29–33.
Deres et al. (1989), Nature 342: 561.

* cited by examiner

Primary Examiner—James Housel
Assistant Examiner—Emily Le
(74) Attorney, Agent, or Firm—Sim & McBurney; Michael I. Stewart

(57) ABSTRACT

Adjuvant compositions for modulating an immune response to an antigen administered to a host comprise a mineral salt adjuvant and at least one other adjuvant. The compositions provide an adjuvanting effect on an antigen which is greater than the adjuvanting effect attainable by one of the adjuvants alone. An antigen is covalently bonded to a glycolipid analog to provide a discrete molecule which exhibits an enhanced adjuvanting effect on the antigen which is greater than the adjuvanting effect attainable in the absence of such covalent bonding.

15 Claims, 9 Drawing Sheets

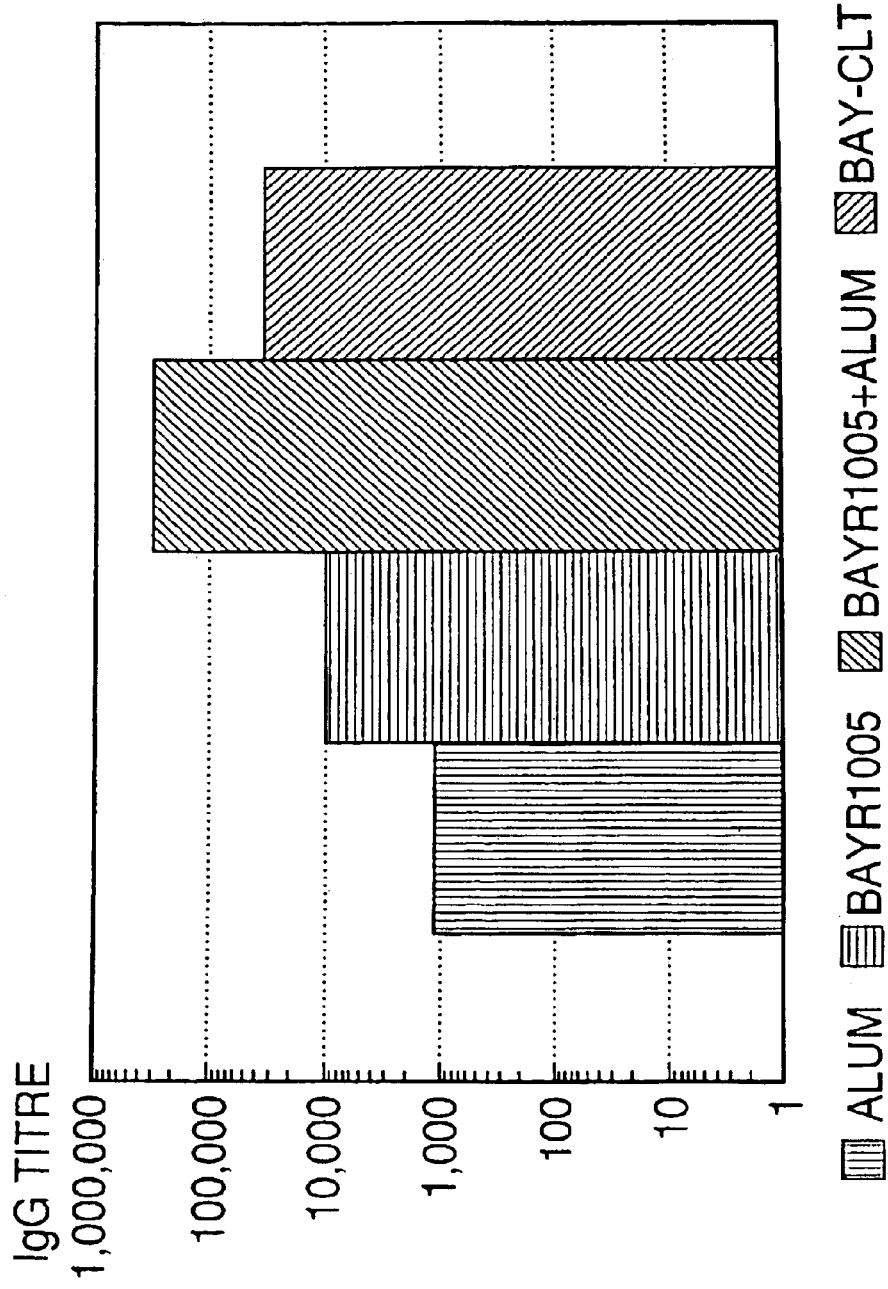

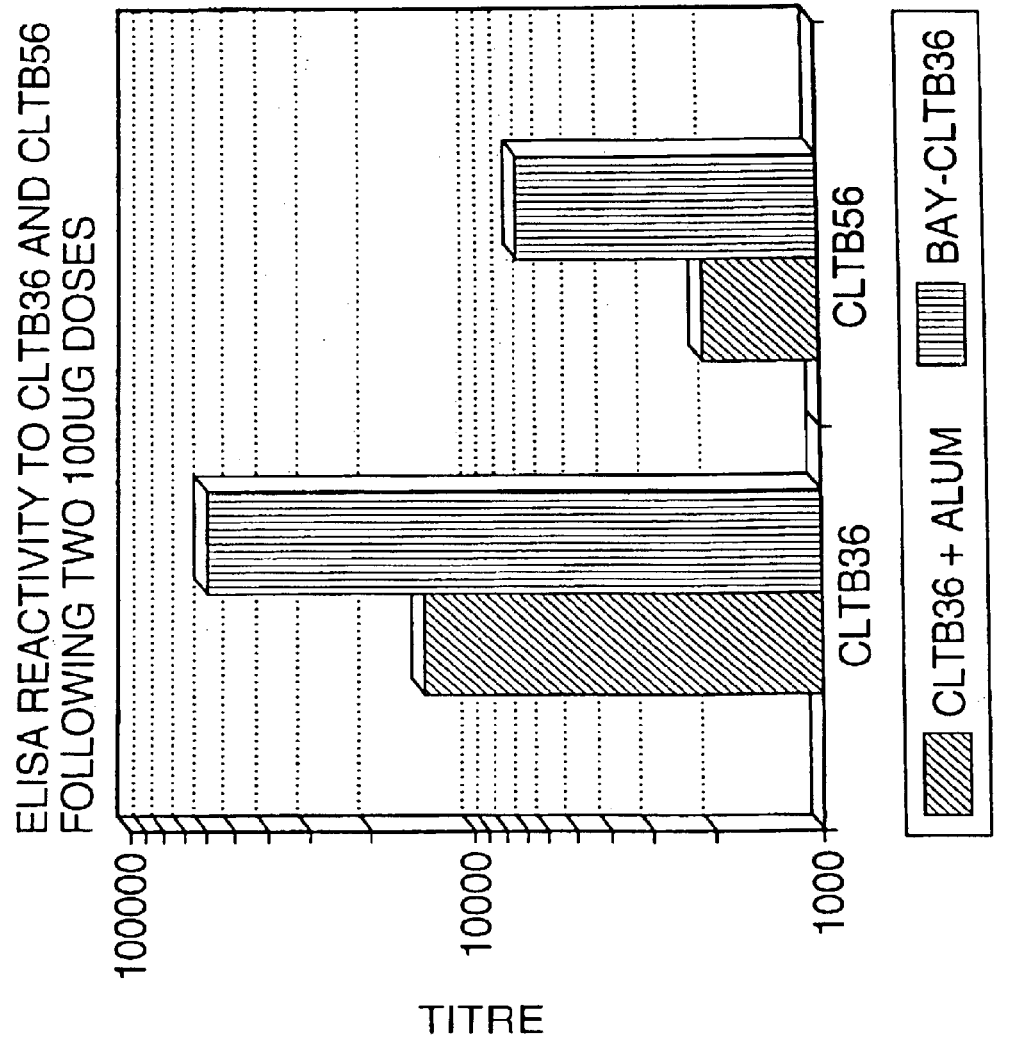

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 33 amino acids
      (B) TYPE: amino acid
      (C) STRANDEDNESS: single
      (D) TOPOLOGY: linear (xi) SEQUENCE DESCRIPTION: SEQ ID NO:1:

```
Gly Pro Lys Glu Pro Phe Arg Asp Tyr Val Asp Arg Phe Tyr Lys Asn
 1               5                  10                  15

Arg Lys Arg Ile His Ile Gly Pro Gly Arg Ala Phe Tyr Thr Thr Lys
                20                  25                  30

Asn
```

(2) INFORMATION FOR SEQ ID NO:2:

(i) SEQUENCE CHARACTERISTICS:
      (A) LENGTH: 33 amino acids
      (B) TYPE: amino acid
      (C) STRANDEDNESS: single
      (D) TOPOLOGY: linear (xi) SEQUENCE DESCRIPTION: SEQ ID NO:2:

Gly Pro Lys Glu Pro Phe Arg Asp Tyr Val Asp Arg Phe Tyr Lys Asn
1               5                   10                  15

Thr Arg Lys Ser Ile Tyr Ile Gly Pro Gly Ala Phe His Thr Thr Gly
            20                  25                  30

Arg (2) INFORMATION FOR SEQ ID NO:3:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:3:

Gly Pro Lys Glu Pro Phe Arg Asp Tyr Val Asp Arg Phe Tyr Lys Asn
1               5                   10                  15

Thr Arg Lys Arg Ile Arg Ile Gln Arg Gly Gly Arg Ala Phe Val Thr
            20                  25                  30

Ile Gly Lys
        35

(2) INFORMATION FOR SEQ ID NO:4:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO:4:

Gly Pro Lys Glu Pro Phe Arg Asp Tyr Val Asp Arg Phe Tyr Lys Asn
1               5                   10                  15

Thr Arg Lys Ser Ile Thr Lys Gly Pro Gly Arg Val Ile Tyr Ala Thr
            20                  25                  30

Gly Gln (2) INFORMATION FOR SEQ ID NO:5:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO:5:

Gly Pro Lys Glu Pro Phe Arg Asp Tyr Val Asp Arg Phe Tyr Lys Asn
1               5                   10                  15

Thr Arg Gln Ser Thr Pro Ile Gly Leu Gly Gln Ala Leu Tyr Thr Thr
            20                  25                  30

Arg Gly (2) INFORMATION FOR SEQ ID NO:6:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO:6:

```
Gly Pro Lys Glu Pro Phe Arg Asp Tyr Val Asp Arg Phe Tyr Lys Ser
1               5                   10                  15

Leu Ile Glu Glu Ser Gln Asn Gln Gln Glu Lys Asn Glu Gln Glu Leu
            20                  25                  30

Leu Glu Leu Asp Lys Trp Ala Ser
        35                  40
```

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO:7:

```
Gln Ser Tyr Ser Ile Met Ser Ile Ile Lys Glu Glu Val Leu Ala Tyr
1               5                   10                  15

Ala Val Gln Leu Pro Leu Pro Leu Tyr Gly Val Ile Asp Thr Pro
            20                  25                  30
```

(2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:8:

```
Pro Ile Val Asn Lys Gln Ser Cys Ser Ile Ser Asn Ile Glu Thr Val
1               5                   10                  15

Ile Glu Phe Gln Gln
            20
```

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:9:

```
Thr Lys Gln Arg Gln Asn Lys Pro Pro Ser Lys Pro Asn Asn Asp Phe
1               5                   10                  15

His Phe Glu Val Phe Asn Phe Val Pro Cys
            20                  25
```

(2) INFORMATION FOR SEQ ID NO:10:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:10:

```
Cys Ser Asn Asn Pro Thr Cys Trp Ala Ile Cys Lys Arg Ile Pro Asn
1               5                   10                  15

Lys Lys Pro Gly Lys Lys Thr
            20
```

(2) INFORMATION FOR SEQ ID NO:11:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:11:

```
Pro Gln Pro Gly Pro Gln Pro Pro Gln Pro Pro Gln Pro Gln Pro Glu
1               5                   10                  15
Ala Pro Ala Pro Gln Pro Pro Cys
            20
```

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:12:

```
Asn Gln Ile Thr Ser Ala Leu Ser Thr Gln Gln Glu Phe Arg Asp Leu
1               5                   10                  15
Lys Lys Tyr Leu Pro Ser Lys Asp Lys Ser Val Val Ser Leu Gln Asp
            20                  25                  30
Arg Ala Cys
        35
```

(2) INFORMATION FOR SEQ ID NO:13:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:13:

```
Thr Val Gly Lys Lys Thr Tyr Gln Val Glu Ala Cys Cys Ser Asn Leu
1               5                   10                  15
Ser Tyr Val Lys Phe Gly Met
            20
```

(2) INFORMATION FOR SEQ ID NO:14:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO:14:

```
Pro Asp Pro Gly Asp Leu Val Glu Tyr Ile Met Asn Tyr Thr Gly Asn
1               5                   10                  15
Gln Gln Ser Arg Trp Gly Leu Gly Ser Pro Asn Cys His Gly Pro Asp
            20                  25                  30
Trp Ala Ser Pro Val Cys Gln Arg His Ser Pro
        35                  40
```

(2) INFORMATION FOR SEQ ID NO:15:

(i) SEQUENCE CHARACTERISTICS:
        (A) LENGTH: 20 amino acids
        (B) TYPE: amino acid -continued

```
          (C) STRANDEDNESS: single
          (D) TOPOLOGY: linear (xi) SEQUENCE DESCRIPTION: SEQ ID NO:15:

Ile Lys Glu Ile Asp Glu Ser Glu Ser Glu Asp Tyr Ala Lys Glu Gly
1               5                  10                  15

Phe Arg Ala Pro
            20

(2) INFORMATION FOR SEQ ID NO:16:

(i) SEQUENCE CHARACTERISTICS:
          (A) LENGTH: 19 amino acids
          (B) TYPE: amino acid
          (C) STRANDEDNESS: single
          (D) TOPOLOGY: linear (xi) SEQUENCE DESCRIPTION: SEQ ID NO:16:

Asn Lys Arg Lys Arg Ile His Ile Gly Pro Gly Arg Ala Phe Tyr Thr
1               5                  10                  15

Thr Lys Asn
```

ADJUVANT COMPOSITIONS CONTAINING MORE THAN ONE ADJUVANT

FIELD OF THE INVENTION

The present invention relates to the field of immunology and is particularly concerned with adjuvants, i.e. materials which modulate immune response to an antigen.

BACKGROUND OF THE INVENTION

Vaccines have been used for many years to protect humans and animals against a wide variety of infectious diseases. Such conventional vaccines consist of attenuated pathogens (for example, polio virus), killed pathogens (for example, *Bordetella pertussis*) or immunogenic components of the pathogen (for example, diphtheria toxoid). Some antigens are highly immunogenic and are capable alone of eliciting protective immune responses. Other antigens, however, fail to induce a protective immune response or induce only a weak immune response.

In the development of some vaccines and immunogenic compositions, there is a trend to use smaller and well defined immunogenic and protective materials. Recent advances in molecular genetics, protein biochemistry, peptide chemistry, and immunobiology have provided economical and efficient technologies to identify and produce large quantities of pure antigens from various pathogens. However, some such materials may not be sufficiently immunogenic, due to either their small size (especially synthetic peptides) or the lack of intrinsic immunostimulatory properties thereof.

Immunogenicity can be significantly improved if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diptheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989 teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (1990), J. Immunology 144:4798–4802 reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller ((1989), Vaccine 7:29–33) describes a peptide with a sequence homologous to a foot-and-mouth disease viral protein coupled to an adjuvant tripalmityl-S-glyceryl-cysteinylserylserine, being a synthetic analogue of the N-terminal part of the lipoprotein from Gram negative bacteria. Furthermore, Deres et al. (1989, Nature 342:561) reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-S-[2,3-bis(palmitylxy)-(2RS)-propyl-[R]-cysteine (TPC).

The adjuvants and immunostimulating compounds described above may not provide for adjuvanticity for all antigens delivered to a variety of hosts under many conditions.

It would be desirable to provide adjuvant compositions that do not suffer from the disadvantages and limitations of currently available adjuvants.

SUMMARY OF INVENTION

The present invention is directed towards the provision of improved adjuvant compositions. In accordance with one aspect of the present invention, there is provided an adjuvant composition for modulating an immune response to an antigen administered to a host, the composition comprising:

(a) a mineral salt adjuvant; and (b) at least one other adjuvant.

The multiple adjuvant compositions provided herein exhibit a surprisingly unexpected adjuvanting effect on an antigen which is greater than the adjuvanting effect attainable by one of the adjuvants alone. The enhanced effect may be additive of the adjuvanting effect of the individual adjuvants and, in particular embodiments, a synergistic effect is attained.

The mineral salt adjuvant preferably comprises aluminum hydroxide or aluminum phosphate, although other known mineral salt adjuvants, such as calcium phosphate, zinc hydroxide or calcium hydroxide, may be used. The at least one other adjuvant may be a glycolipid analog, an octadecyl ester of an amino acid (such as an aromatic amino acid) or a lipoprotein. The lipoprotein may be a synthetic analogue of an N-terminal portion of lipoprotein.

In a particular embodiment, the glycolipid may be a glycosylamide and may have the formula:

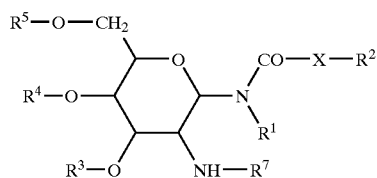

(I)

wherein R1 denotes hydrogen or saturated or singly or multiply unsaturated alkyl radical having up to 50 carbon atoms;

X represents —$CH_2$—, —O— or —NH—;

R2 denotes hydrogen or a saturated or singly or multiply unsaturated alkyl radical having up to 50 carbon atoms, R3, R4, and R5, independently of one another, denotes hydrogen, or $SO_4^{2-}$, or $PO_4^{2-}$, or other negatively charged moiety, or —CO—R6, R6 being an alkyl radical having up to 10 carbon atoms;

R7 is L-alanyl, L-alpha-aminobutyryl, L-arginyl, L-asparginyl, L-aspartyl, L-cysteinyl, L-glutamyl, L-glycyl, L-histidyl, L-hydroxypropyl, L-isoleucyl, L-leucyl, L-lysyl, L-methionyl, L-ornithinyl, L-phenylalanyl, L-prolyl, L,-seryl, L-threonyl, L-tyrosyl, L-tryptophanyl, and L-valyl or their D-isomers;

and pharmaceutically acceptable salts thereof. In an embodiment, the glycosylamide may be N-(2-deoxy-2-L-leucylamino-β-D-glucopyranosyl)-N-octadecyldodecanamide acetate.

In accordance with a further aspect of the present invention, there is provided an immunogenic composition for eliciting an immune response in a host, including a human, the composition comprising:

(a) at least one antigen;

(b) a mineral salt adjuvant; and (c) at least one other adjuvant.

In yet another aspect of the invention, there is provided a method of modulating an immune response to an antigen comprising combining the antigen with the adjuvant composition of the present invention.

Convenient antigens which may be included in said immunogenic compositions and in respect of which an immune response is modulated, include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

Such peptides, glycopeptides or lipopeptides may include an amino acid sequence corresponding to an antigenic determinant of HIV, Rubella virus, Respiratory Syncytial Virus, *Bordetella pertussis, Haemophilus influenzae* or *Streptococcus pneumoniae*, including those specific synthetic peptides shown in Table I below (SEQ ID NOS: 1 to 15) (The Tables appear at end of the descriptive text) or a functional analog thereof. The toxoid may be a pertussis toxoid while the protein may be influenza hemagglutinin or a parainfluenza virus subunit, such as the HN or F proteins of PIV-3.

In a further aspect of the invention, there is provided a method of generating an immune response in a host, including a human, comprising administering thereto the immunogenic composition of the present invention. The immune response attained may be a humoral or a cell-mediated immune response.

In a particular aspect of the present invention, there is provided a kit for preparing an immunogenic composition, comprising:

(a) means for containing a mineral salt adjuvant;

(b) means for containing at least one other adjuvant;

(c) means for containing at least one antigen; and (d) means for combining the mineral salt adjuvant, at least one other adjuvant and at least one antigen to produce the immunogenic composition.

In a further aspect of the present invention, there is provided a compound comprising an antigen, including any of those referred to above, covalently linked to a glycolipid analog, such as a glycosylamide, as well as immunogenic compositions comprising the same for generating an immune response in a host, including a human. The glycosylamide may have the formula I above.

By covalently bonding an antigen to a glycolipid analog, a discrete molecule is produced which exhibits a surprisingly unexpected enhanced adjuvanting effect on the antigen which is greater than the adjuvanting effect attainable in the absence of such covalent bonding, as in a mixture of the two components. A further enhanced adjuvanting effect may be attained for such covalently-bonded antigen by incorporating a mineral salt adjuvant with such compounds.

The antigen may be covalently linked to the glycolipid analog at a carboxy or amino terminus or other suitable site compatible with covalent linkage of the antigen by, for example, a cross-linker having a reactive function, such as maleimidyl, succinimidyl, 2-pyridyldithio, $NH_2$, SH, and —CO—R8, where R8 is —OH, $N_3$, —O-alkyl($C_1$–$C_2$), —$OC_6F_5$, H, Br, or Cl.

Advantages of the present invention include:
(a) ease of formulation;
(b) effectiveness of adjuvanticity; and
(c) compatibility of antigens with the adjuvant composition.

BRIEF DESCRIPTION OF THE DRAWINGS

FIG. 8 shows a guinea pig immune response to an HIV peptide CLTB36 formulated with adjuvants or conjugated to BAY R1005 according to an embodiment of the present invention; and FIG. 9 shows guinea pig antibody responses to HIV peptide (CLTB 36) formulated with alum or conjugated to BAY R1005 according to an embodiment of the present invention.

GENERAL DESCRIPTION OF THE INVENTION

Figure 1:
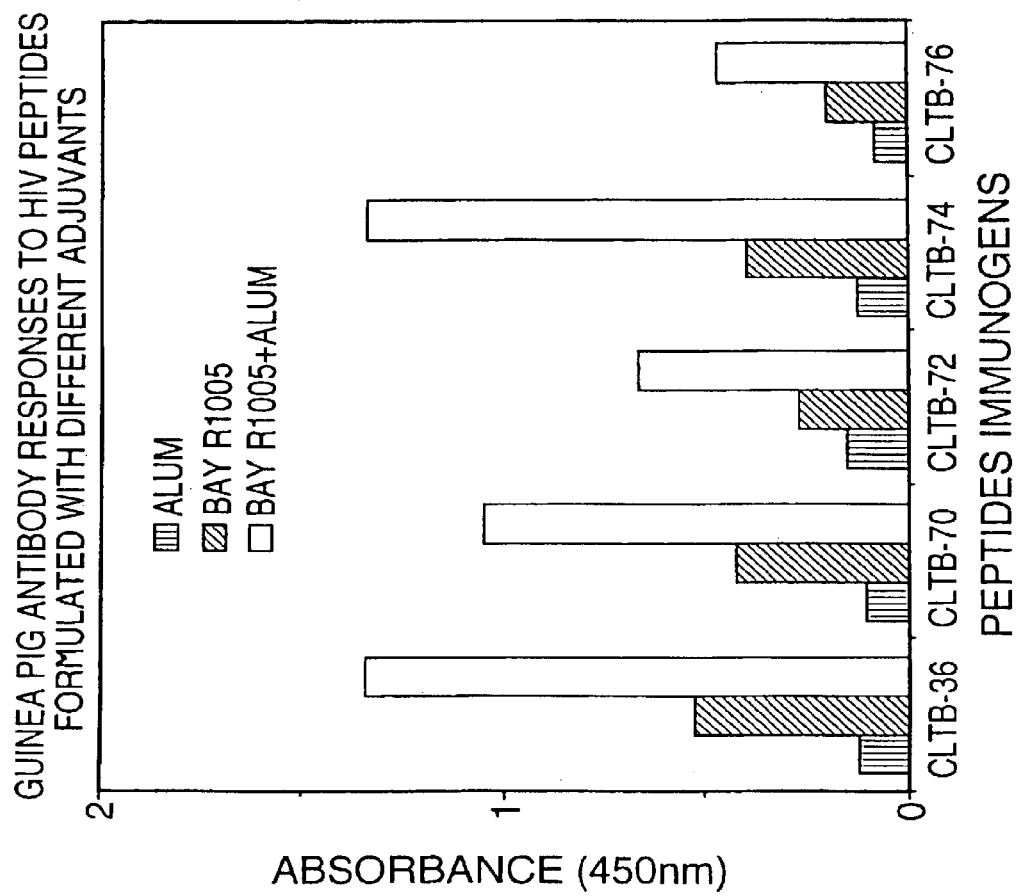
FIG. 1 shows antibody responses to HIV peptides in guinea pigs formulated with adjuvants according to one embodiment of the invention.
Figure 2:
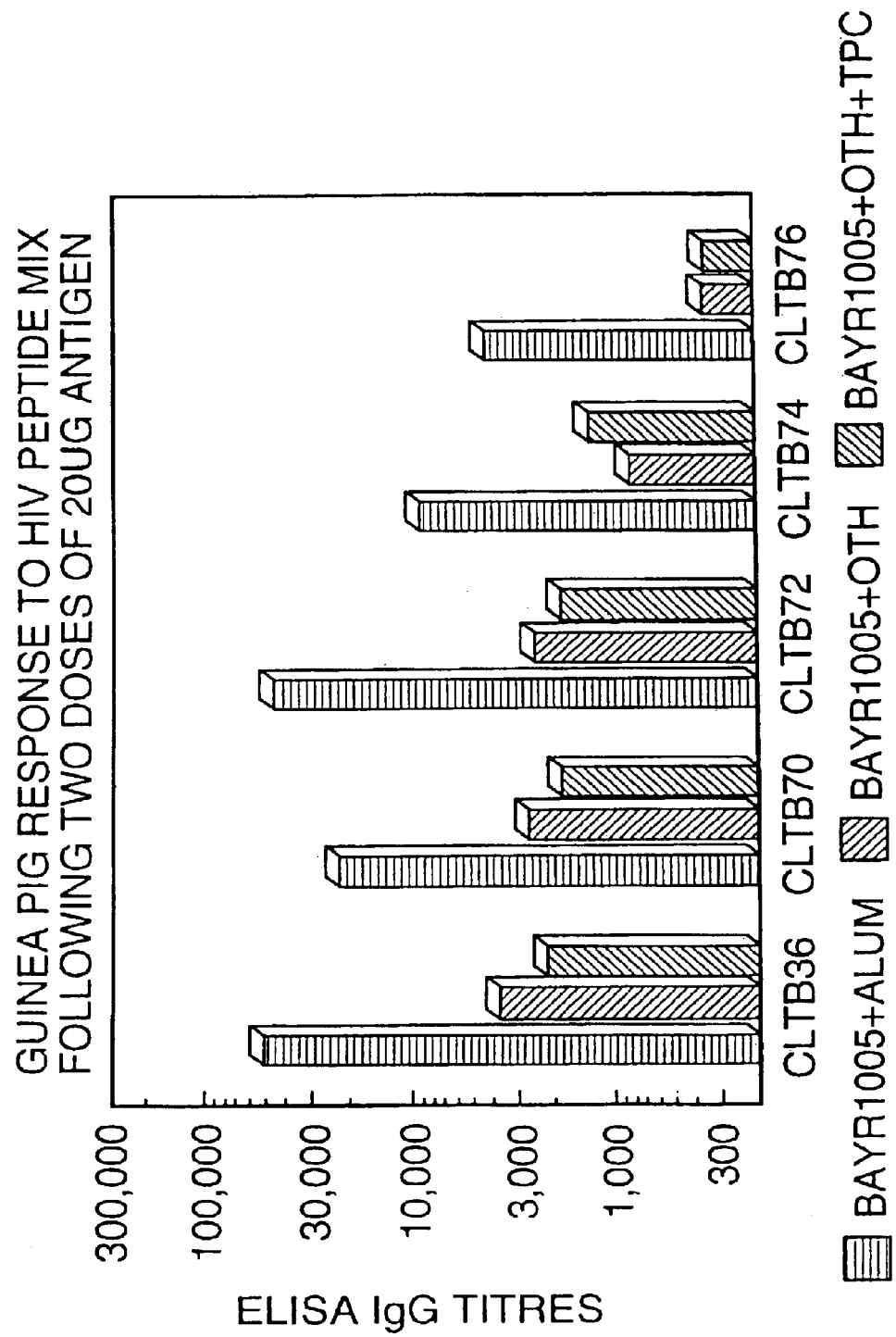
FIG. 2 shows antibody responses in guinea pigs to a cocktail of HIV peptides formulated with adjuvants according to an embodiment of the present invention.

It will be apparent to those skilled in the art, that the various embodiments of the present invention have many applications in the fields of medicine and, in particular, vaccination, diagnosis, generation of immunological agents, and treatment of infections with pathogens, including bacteria and viruses. A further non-limiting discussion of such uses is further presented below.

As noted above, the present invention relates, in one aspect, to adjuvant compositions useful for modulating the immune response to an antigen.

Synthetic antigens, including vaccines, may be prepared by chemically synthesizing peptides sharing antigenic determinants with proteins, for example, of HIV-1, rubella virus, RSV, *Haemophilus influenzae* type b, *Bordetella pertussis* and *Streptococcus pneumoniae* or other antigens. These peptides, lipid derivatives of such peptides as well as viral antigens or bacterial antigens, may be used either individually or combined as a cocktail, and formulated with synthetic adjuvants and mineral salts to provide an immunogenic composition. These compositions can be used to immunize mammals, for example, by the intramuscular or parenteral routes, or by delivery to mucosal surfaces using microparticles, capsules, liposomes and targeting molecules, such as toxins and antibodies.

Reference will now be made in detail to the presently preferred embodiments of the invention, which together with the following Examples, help to explain the invention.

Antigen Selection

Several antigens were selected to exemplify the present invention. Advances in biotechnology now enable bacterial and viral antigens to be identified and purified on a large scale. However, subunit or synthetic vaccine candidates are sometimes of low immunogenicity, due to their size (especially synthetic peptides) or the lack of intrinsic immunostimulatory properties. Thus, external additives are often required to enhance their immunogenicity. Several antigens have been chosen which are able to elicit strong IgG antibody responses in adjuvants, such as CFA. The selected antigens include synthetic peptides (Table 1) sharing antigenic determinants with the proteins of HIV-1, rubella virus (RV), respiratory syncytial virus (RSV), *Haemophilus influenzae* type b (Hib), *Bordetella pertussis* and *Streptococcus pneumoniae*, and the HN and F proteins from parainfluenza virus 3 (PIV3), pertussis toxoid and chemically-disrupted influenza virus.

Synthetic Adjuvants

Synthetic adjuvants, such as glycolipid analogs (Lockhoff et al., U.S. Pat. No. 4,855,283), lipopeptide (Wiesmuller et al. (1989), Vaccine 7:29–33) and octadeyl ester of aromatic amino acids (Moloney et al., U.S. Pat. No. 4,258,029) have been shown to act as adjuvants to enhance the immunogenicity of viral and bacterial antigens. Therefore, three adjuvants, namely N-palmityl-S-[2,3-bis(palmityloxy)-(2RS)-propyl-[R]-cysteine (TPC, Wiesmuller et al., Vaccine (1989) 7:29–33); N-(2-deoxy-2-L-leucylamino-β-D-glucopyranosyl)-N-octadecyldodecanamide acetate (BAY R1005, O. Lockhoff, Angew. Chem. Int. Ed. Engl. (1991) 30:1611–1620); and octadecyl-tyrosine (OTH) (Nixon-George et al. (1990), J. Immunology 144:4798–4802) were selected as starting molecules for designing more potent synthetic adjuvant compositions. These three classes of synthetic adjuvants were synthesized and characterized. The synthesis of the three classes of adjuvants required less than ten steps of reaction. The protocols for the adjuvant synthesis are well established and reported in the literature. Scale-up production for BAY R1005 and octadecyl-tyrosine would be within the skill of the art.

All three classes of synthetic adjuvant are insoluble in water or aqueous buffer, such as phosphate buffered saline (PBS). They form a milky solution when mixed with water or aqueous buffer. They are non-toxic, as judged by a lack of adverse reactions in mice injected with 1 to 2 mg, and non-pyrogenic in a rabbit pyrogen test. All three classes of synthetic adjuvant are very stable in powdered form at −20° C. and can be suspended into aqueous buffer for long term storage at 4° C.

To analyse the effectiveness of the synthetic adjuvants, 100 µg of synthetic peptides (Table 1) containing known functional T-helper and B-cell epitopes were used as antigens. Fifteen peptides, including epitopes from HIV-1, RSV, Rubella virus, *H. influenzae, B. pertussis*, and *S. pneumoniae*, were individually injected intramuscularly into guinea pigs, either in the presence of FCA, or alum (aluminium phosphate), or TPC, or BAY R1005, or OTH or PBS. The effect of adjuvants on antibody responses were evaluated using peptide-specific ELISAs. As shown in Table 2 below, all peptides emulsified in FCA elicited strong antibody responses, whereas peptides in PBS either elicited very low anti-peptide titer or failed to elicit any detectable antibody response. After three immunizations, the fifteen peptides absorbed onto alum were capable of inducing peptide-specific IgG antibody responses. Only two peptides (RV-EP27 and PSP-AA) in the presence of BAY R1005, failed to elicit significant antibody responses after three immunizations. One of the peptides (RV-EP27) that failed to elicit significant antibody responses in BAY R1005, was highly immunogenic and induced peptide-specific antibody response when TPC was used as adjuvant. In most cases, both synthetic adjuvants, TPC and OTH, enhanced the immunogenicity of the peptide, but the reactive titers were much lower than those obtained from alum or CFA. These results are consistent with published data reported by other workers, and demonstrate the adjuvant potential of the synthetic adjuvants and the capacity of these peptides to be adjuvanted.

In one aspect, the present invention provides an adjuvant composition for modulating an immune response to an antigen administered to a host, the composition comprising a mineral salt adjuvant and at least one other adjuvant. To exemplify this aspect of the invention, several HIV-1 peptides were used in guinea pig immunogenicity studies. Peptides were absorbed onto alum first and then emulsified with the synthetic adjuvant before injecting into different groups of guinea pigs. Guinea pigs were also immunized either with peptides absorbed onto alum, or peptides emulsified with synthetic adjuvant, as controls. The antibody response results obtained with the synthetic adjuvant BAY R1005 are shown in FIG. 1. No adverse reactions were seen in any of the guinea pigs. It was surprisingly found, according to the present invention, that alum (3 mg/mL) combined with a synthetic adjuvant (BAY R1005 (1 mg/mL)) resulted in increased anti-peptide antibody responses after two immunizations in comparison to those titers produced by the same peptide using either synthetic adjuvant or mineral salts alone as adjuvant. These studies thus indicate that the immune response to an antigen that has already been enhanced by adsorption to alum under standard conditions can unexpectedly be further enhanced by another adjuvant, according to the present invention.

The unexpected immune response enhancing capacity of adjuvant compositions of the present invention was further demonstrated for synthetic peptides RSV-F and RV-EP27 (Table 1). When these peptides were adjuvanted with alum alone, antibody titres of 32000 (RSV-F) and 12800 (RV-EP27) were obtained (Table 3). When the same peptides were adjuvanted with BAY R1005, they were poorly immunogenic. However, when these peptides were adjuvanted with an adjuvant composition comprising alum and BAY R1005, antibody titres of 128,000 (RSV-F) and 64000 (RV-EP27) were obtained. These results thus show the capacity of this adjuvant composition to enhance the immune response to an antigen beyond that obtainable by either individual adjuvant. In fact, an immune response was obtained that was more than the sum of the immune response to each of the adjuvants individually, i.e. a synergistic effect was obtained.

Figure 3:
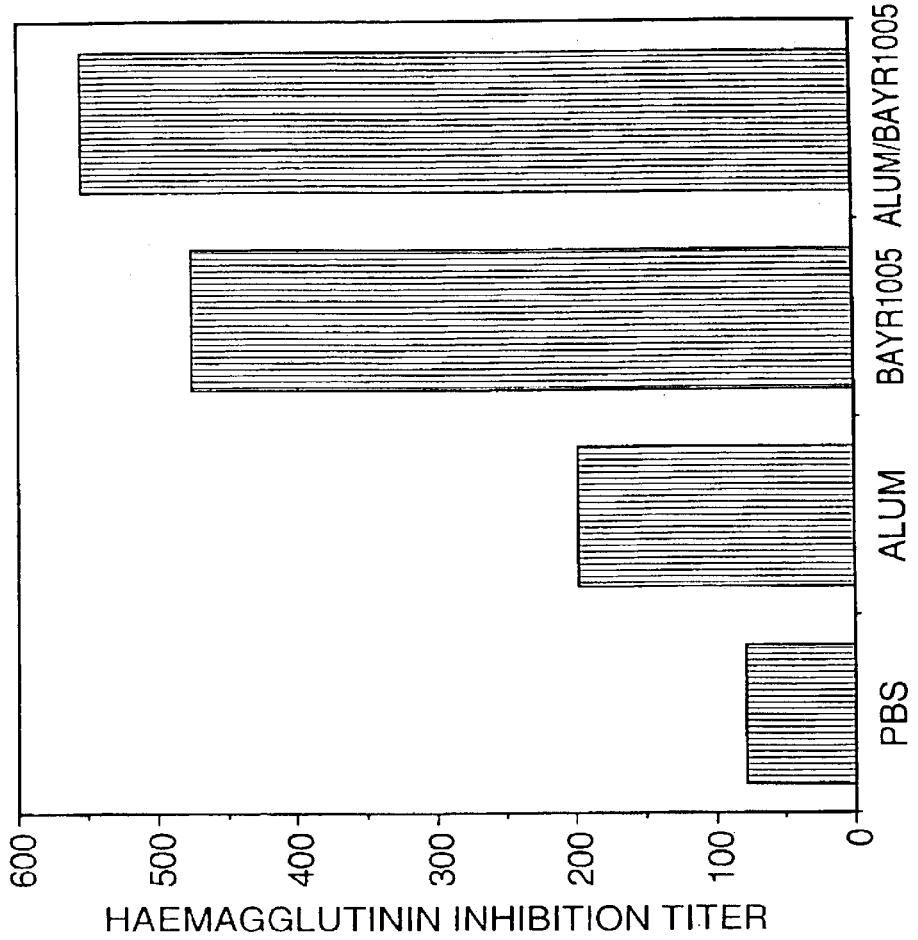
FIG. 3 shows haemagglutinin inhibition antibody responses in mice to a Human parainfluenza virus subunit vaccine formulated with adjuvants according to the present invention.
Figure 4:
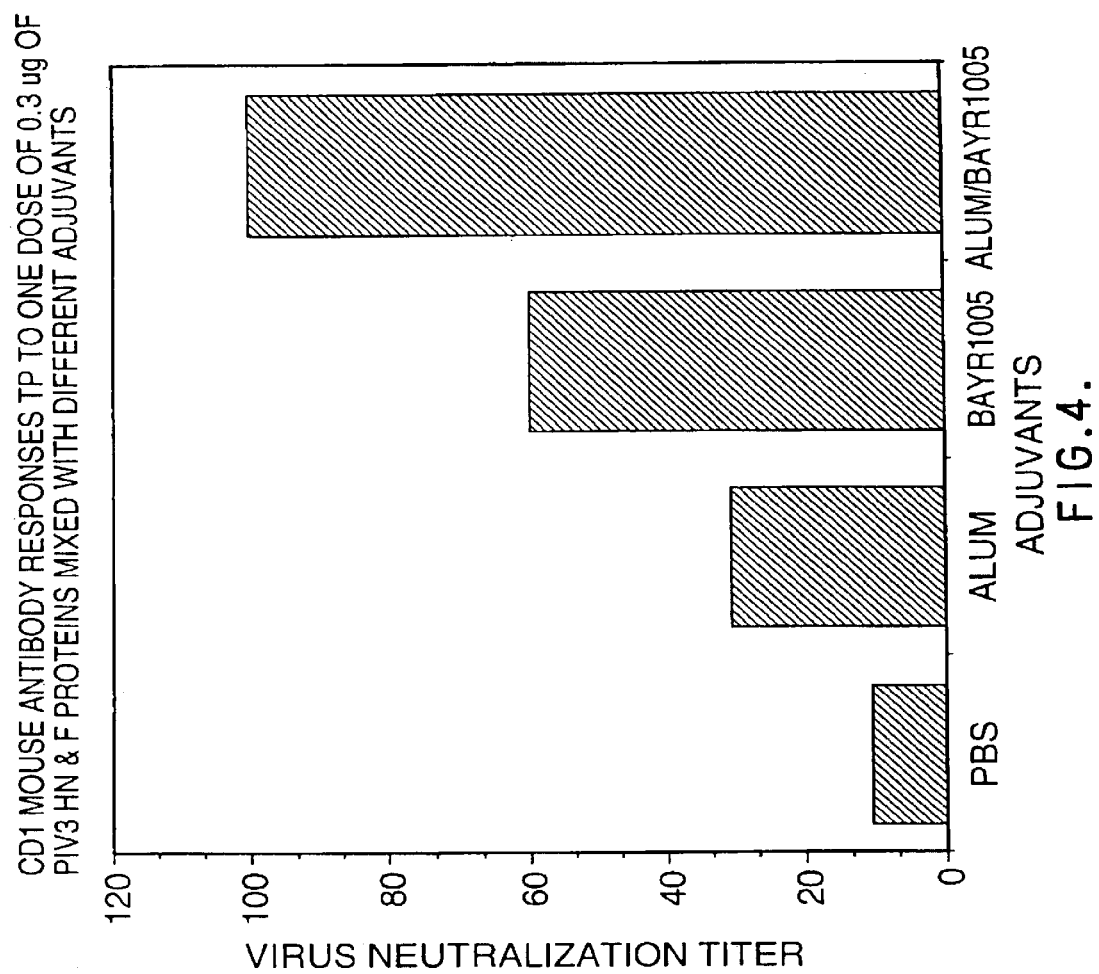
FIG. 4 shows virus neutralization antibody responses to a Human parainfluenza virus subunit vaccine formulated with adjuvants according to the present invention.

To further assess the adjuvant effect of the present invention, the HN and F glycoproteins from parainfluenza virus 3 (PIV3) were absorbed first onto alum and then emulsified with BAY R1005 before injecting intraperitoneally (i.p.) to CD1 mice. As controls, the same antigens were either absorbed onto alum, or emulsified with BAY R1005, or mixed with PBS and then used to immunize i.p. groups of CD1 mice. No adverse reactions were seen in any of the mice. It was surprisingly found that the primary antibody responses to HN and F were best with the alum/BAY R1005 adjuvant composition. The functional antibody responses as measured by haemagglutinin inhibition and virus neutralization assays, revealed that mice immunized with antigen formulated with an adjuvant composition of the present invention generated higher antibody levels than obtained with a single adjuvant (FIGS. 3 and 4).

Figure 5:
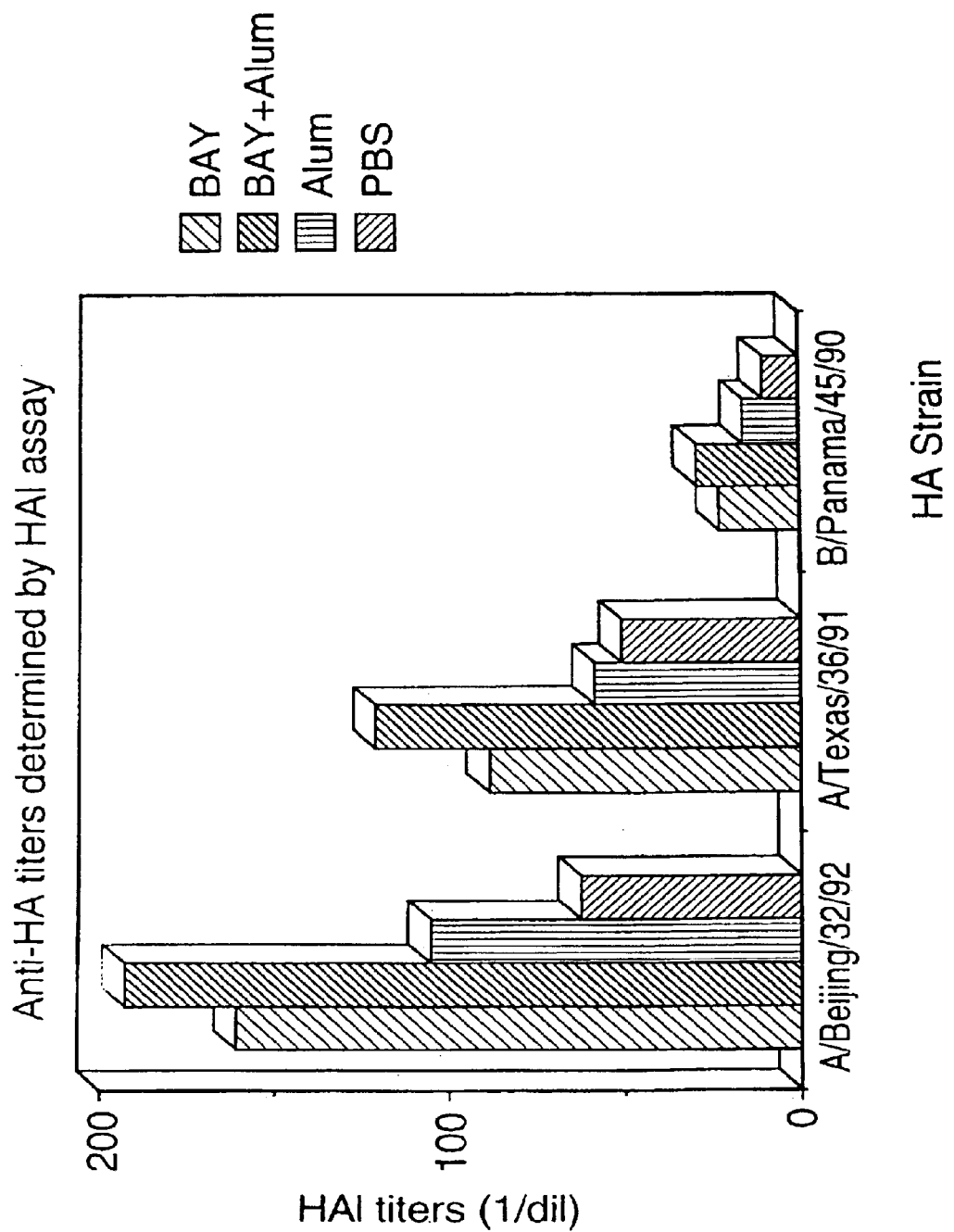
FIG. 5 shows guinea pig immune responses to a split influenza vaccine formulated with adjuvants according to an embodiment of the present invention against three influenza virus strains.

To determine whether the steps of formulation would affect the adjuvant effects of the compositions of the present invention, commercially-available split flu vaccine was first emulsified with BAY R1005 (1 mg/mL) and then absorbed onto alum (3 mg/mL) before injecting intraperitoneally (i.p.) into mice. As controls, the same preparation was either absorbed onto alum, or emulsified with BAY R1005, or mixed with PBS and then was used to immunize different groups of mice. Again, no adverse reactions were seen in any of the groups of mice. The BAY R1005/alum combination adjuvant formulation gave the best anti-HA antibody responses (FIG. 5) against various influenza strains.

The results obtained with the split flu vaccine indicate that the sequence of steps used to formulate the antigen with the different adjuvants is not material to the adjuvanting effect obtained.

Figure 6:
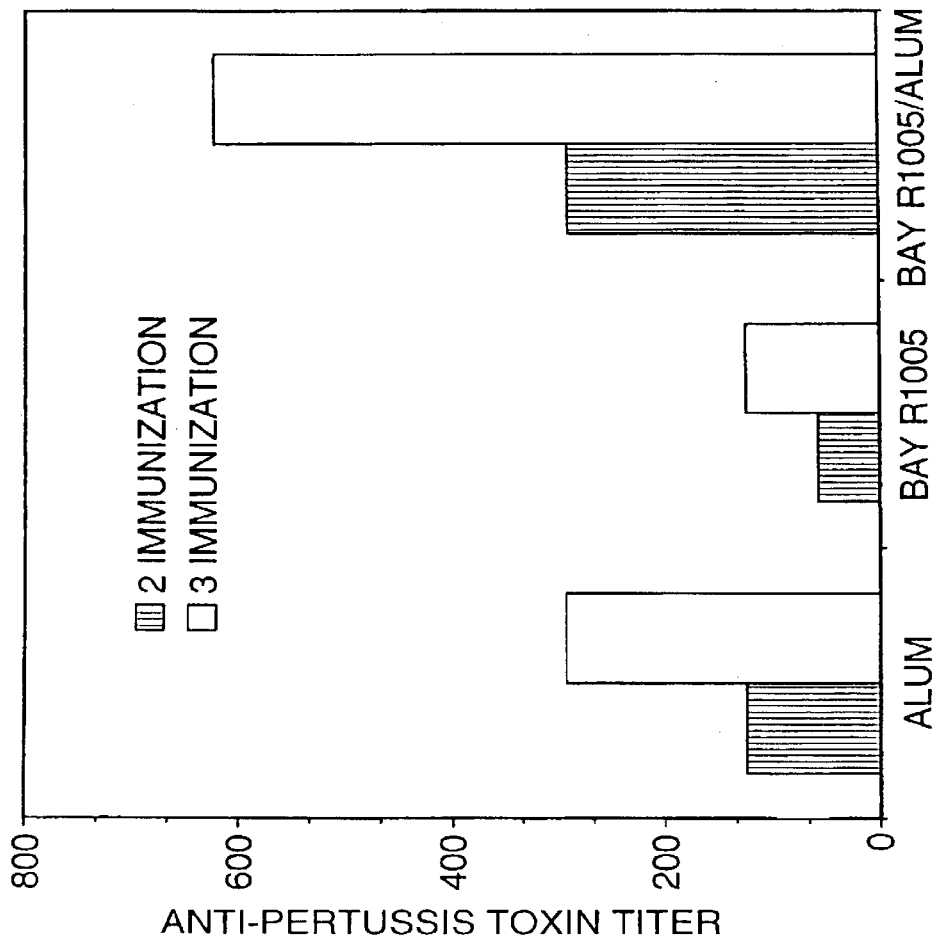
FIG. 6 shows guinea pig immune responses (determined by anti-PT ELISA) to pertussis toxoid formulated with adjuvants according to an embodiment of the present invention.
Figure 7:
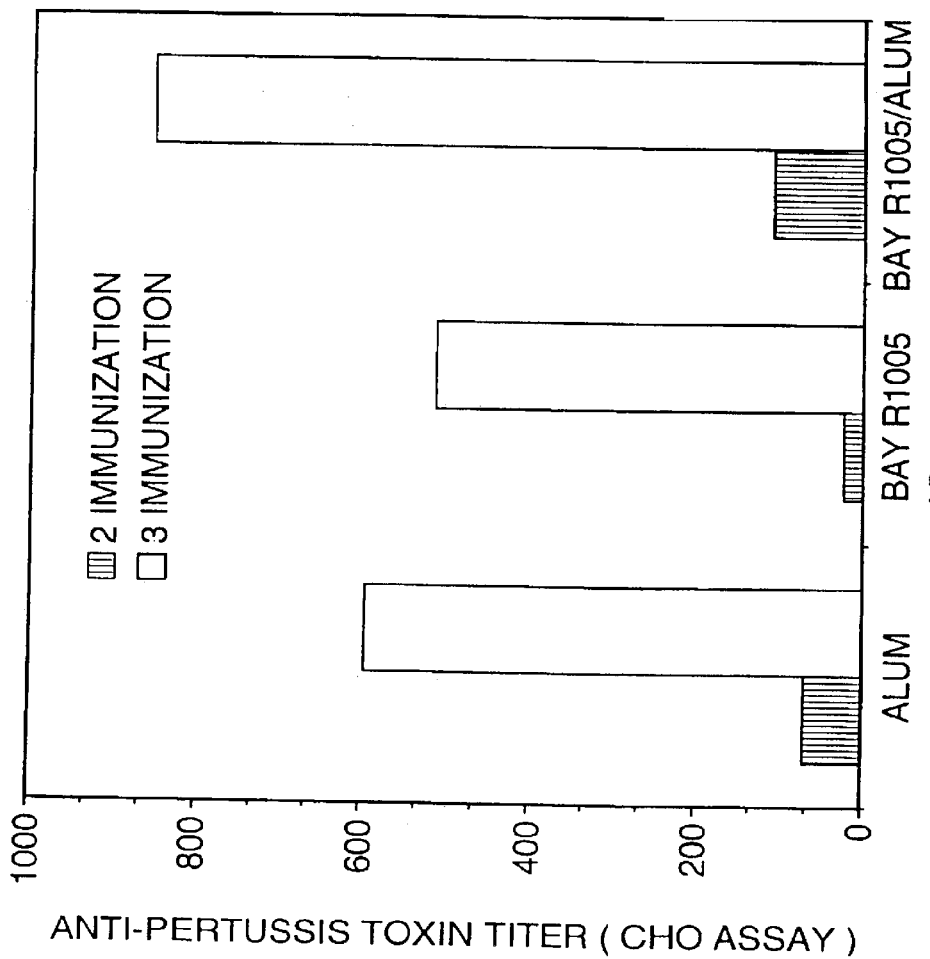
FIG. 7 shows guinea pig immune responses (determined by the CHO cell neutralizing assay) (Grunstrom et al. 1985 J. Infec. Dis. 151:646–649) to pertussis toxoid formulated with adjuvants according to an embodiment of the present invention.

The adjuvant compositions of the present invention were also able to modulate the immune response to gluteraldehyde-inactivated pertussis toxoid. Thus, guinea pigs were immunized with pertussis toxoid in alum alone, BAY R1005 or BAY R1005 anti-PT and toxin neutralizing antibody titres determined (FIGS. 6 and 7). The results presented indicate that the highest (and a synergistic) immune response was obtained when the pertussis toxoid was formulated with alum and BAY R1005 according to the present invention.

Imunogenicity of Peptides Covalently Linked to Synthetic Adjuvants

The task of providing a synthetic peptide as a self-sufficient immunogen capable of eliciting both humoral and cell-mediated immune responses, is very challenging. To determine whether a peptide antigen covalently linked to an adjuvant can elicit both humoral and cell-mediated immune responses, peptide CLTB-36 was synthesized with synthetic adjuvant BAY R1005 covalently linked at the N-terminus. During the preparation of the CLTB-36 covalently linked with BAY R1005, it may be desirable to use Fmoc peptide synthesis chemistry and temporarily protect reactive functional groups, for example, alcohols by t-butyl and acids by ester groups. Suitable protection-deprotection conditions and protocols are described in Examples herein. The peptide-adjuvant conjugate was purified by RP-HPLC and used to immunize guinea pigs. These immunogenicity studies revealed that CLTB-36 covalently linked to BAY R1005 was as immunogenic as CLTB-36 formulated with (BAY R1005+alum) (FIGS. 8, 9 and Table 4). The anti-CLTB-36 antibody titer obtained was about 3-fold and 20-fold higher than those elicited either in the presence of BAY R1005 or alum, respectively (FIG. 8). In addition, the peptide-adjuvant conjugate (BAY-CLTB-36) required fewer immunizations and less antigen to elicit the same degree of anti-peptide antibody responses as shown in FIG. 9. These results show that an antigen with a built-in immunomodulator can induce strong immune responses.

Vaccine Preparation and Use

As indicated above, the present invention, in one embodiment, provides adjuvant mixtures useful for formulating immunogenic compositions, suitable to be used as, for example, vaccines. The immunogenic composition elicits an immune response by the host to which it is administered including the production of antibodies by the host. The immunogenic compositions include at least one antigen in one embodiment. This antigen may be an inactivated pathogen or an antigenic fraction of a pathogen. The pathogen may be, for example, a virus, a bacterium or a parasite. The pathogen may be inactivated by a chemical agent, such as formaldehyde, glutaraldehyde, β-propiolactone, ethyleneimine and derivatives, or other compounds. The pathogen may also be inactivated by a physical agent, such as UV radiation, gamma radiation, "heat shock" and X-ray radiation.

An antigenic fraction of a pathogen can be produced by means of chemical or physical decomposition methods, followed, if desired, by separation of a fraction by means of chromatography, centrifugation and similar techniques. In general, low molecular components are then obtained which, although purified, may have low immunogenicity. Alternatively, antigens or haptens can be prepared by means of organic synthetic methods, or, in the case of, for example, polypeptides and proteins, by means of recombinant DNA methods.

Vaccines containing peptides are generally well known in the art, as exemplified by U.S. Pat. Nos. 4,601,903; 4,599,231; 4,599,230; and 4,596,792; all of which references are incorporated herein by reference.

The use of peptides in vivo may first require their chemical modification since the peptides themselves may not have a sufficiently long serum and/or tissue half-life and/or sufficient immunogenicity.

For this purpose, the molecule of the invention may optionally be linked to a carrier molecule. Many suitable linkages are known, e.g., using the side chains of the Tyr residues. Suitable carriers include, e.g., keyhole limpet hemocyanin (KLH), serum albumin, purified protein derivative of tuberculin (PPD), ovalumin, non-protein carriers and many others.

In addition, it may be advantageous to modify the peptides in order to impose a conformational restraint upon them. This might be useful, for example, to mimic a naturally-occurring conformation of the peptide in the context of the native protein in order to optimize the effector immune responses that are elicited.

Modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

It will be apparent that the peptides employed herein as antigens can be modified in a variety of different ways without significantly affecting the functionally important immunogenic behaviour thereof. Possible modifications to the peptide sequence may include the following:

One or more individual amino acids can be substituted by amino acids having comparable or similar properties, thus:

V may be substituted by I;

T may be substituted by S;

K may be substituted by R; or

L may be substituted by I, V or M.

One or more of the amino acids of peptides of the invention can be replaced by a "retro-inverso" amino acid, i.e., a bifunctional amine having a functional group corresponding to an amino acid, as discussed in published International application WO 91/13909.

One or more amino acids can be deleted.

Structural analogs mimicking the 3-dimensional structure of the peptide can be used in place of the peptide.

Examples of side chain modifications contemplated by the present invention include modification of amino groups, such as by reductive alkylation by reaction with an aldehyde followed by reduction with $NaBH_4$; amidation with methylacetimidate; acetylation with acetic anhydride; carbamylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents, such as 2,3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altred by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-mehtylheptanoic acid, 2-thienyl alanine and/or D-isomers of amino acids.

The immunogenic compositions may be prepared as injectables, as liquid solutions or emulsions. The antigens and immunogenic compositiions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

These compositions may take the form of solutions, suspensions, tablets, pills, capsules, sustained release formulations or powders and contain 1 to 95% of the immunogenic compositions of the present invention.

The immunogenic compositions are administered in a manner compatible with the dosage formulation, and in such amount as to be therapeutically effective, protective and immunogenic. The quantity to be administered depends on the subject to the immunized, including, for example, the capacity of the subject's immune system to synthesize antibodies, and if needed, to produce a cell-mediated immune response. Precise amounts of antigen and immunogenic composition to be administered depend on the judgement of the practitioner. However, suitable dosage ranges are readily determinable by those skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

The concentration of antigen in an immunogenic composition according to the invention is in general 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunoassays

In one embodiment, the adjuvant mixtures of the present invention are useful for the production of immunogenic compositions that can be used to generate antigen-specific antibodies that are useful in the specific identification of that antigen in an immunoassay according to a diagnostic embodiment. Such immunoassays include enzyme-linked immunosorbent assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a colour development upon incubating with an appropriate chromogenic substrate. Quantification may then achieved by measuring the degree of colour generation using, for example, a visible spectra spectrophotometer. In an additional embodiment, the present invention includes a diagnostic kit comprising antigen-specific antibodies generated by immunization of a host with immunogenic compositions produced according to the present invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes the preparation of synthetic peptides.

Peptides (Table 1) were synthesized using an ABI 430A peptide synthesizer and optimized t-Boc chemistry as described by the manufacturer, then cleaved from the resin by hydroflouric acid (HF). The peptides were purified by reversed-phase high performance liquid chromatography (RP-HPLC) on a Vydac C4 semi-preparative column (1×30 cm) using a 10 to 50% acetonitrile gradient in 0.1% trifluoryl acetic acid (TFA) developed over 40 minutes at a flow rate of 2 mL/min. All synthetic peptides (Table 1) were >95% pure as judged by analytical HPLC. Amino acid composition analyses of these peptides performed on a Waters Pico-Tag system were in good agreement with their theoretical compositions.

Example 2

This Example describes the synthesis of adjuvants.

N-alkyl-N-glycosyl-carboxamides (N-(2-L-leucine-amino-2-deoxy-β-D-glucopyranosyl)-N-octadecyl-dodecanoic acid amide, BAY R1005 and its analogs) were prepared following the process disclosed in Lockhoff et al., U.S. Pat. No. 4,855,283. BAY R1005 and its analogs can be further purified by ion-exchange chromatography. The octadeyl ester of an aromatic amino acid (OTH) was prepared according to Moloney et al., U.S. Pat. No. 4,258,029. Fmoc-S-(2,3-bis(palmitoyloxy)-[2R]-propyl)-[R]-cysteine using the coupling procedure of Fmoc chemistry into a growing peptide chain and then acylated at the N-terminus by a palmityl group. TPC derivatives can be either tripalmityl-Cys-Ser-Ser-Asn-Ala (Ad) or tripalmityl-Cys-Ser-Glu-Glu-Glu-Glu (Ad-4), or tripalmityl-Cys-Ser-Lys-Lys-Lys-Lys (Ad-2).

Example 3

This Example describes the formulation of adjuvants with an antigen.

The adjuvant BAY R1005, OTH or TPC derivatives were mixed with sterile distilled water or saline buffer using for example a sonicator for two to thirty minutes. The adjuvants were prepared on a laboratory scale as stock solutions of 10 mg/mL for BAY R1005, 1 mg/mL for OTH and TPC derivatives. The synthetic adjuvant stock solution was added to an antigen to produce 1 mg/mL BAY R1005 or 200 μg/mL OTH or TPC derivatives. The antigen may be obtained by, for example, methods of peptide synthesis and recombinant techniques that are not explicitly described in this disclosure but are amply reported in the scientific literature and are within the scope of those skilled in the art.

Example 4

This Example describes the preparation of adjuvant compositions and immunogenic compositions containing a mineral salt adjuvant and at least one other adjuvant.

A synthetic adjuvant may be prepared as described in Example 2 and the mineral salt adjuvant may be clinical grade aluminum phosphate obtainable from, for example, Connaught Laboratories Limited, Toronto Canada.

The immunogenic composition was prepared by first mixing BAY R1005 with sterile distilled water or saline buffer using a sonicator for two to thirty minutes. Ten mL of the desired amount (1 to 200 μg per mL) of antigen absorbed onto 3.1 mg per mL of $AlPO_4$ suspension for 1 to 24 hr, was added to 1 mL BAY R1005 stock solution, and the solution was mixed gently for 30 minutes at room temperature.

Preparation of an HIV Synthetic Peptide Immunogenic Composition

A BAY R1005 stock solution of 10 mg/mL was prepared as described above. Ten mL of the desired amount (20 to 200 μg per mL) of HIV synthetic peptides (Table 1) absorbed onto 3.1 mg per mL of $AlPO_4$ suspension for 1 to 24 hr, were then added to 1 mL BAY R1005 stock solution, and the solution mixed gently for 30 minutes at room temperature. The HIV synthetic peptide vaccine formulation was stored at 4° C. for long term storage. The vaccine formulation was gently mixed for 10 minutes at room temperature before injecting into hosts.

Preparation of a Flu Vaccine Formulation

A BAY R1005 stock solution of 10 mg/mL was prepared as described above. Ten mL solution containing twenty human doses of flu split vaccine obtained commercially from Pasteur Merieux SV, Lyon, France, were added into 1 mL BAY R1005 stock solution. The mixture was vortexed for 10 minutes at room temperature. The emulsified flu vaccine was then mixed with 3.1 mg per mL of $AlPO_4$ suspension for 1 to 24 hr, and then the vaccine formulation stored at 4° C.

Preparation of RSV Pentide Vaccine Formulation

A BAY R1005 stock solution of 10 mg/mL was prepared as described above. Ten mL of the desired amount (100 μg per mL) of RSV synthetic peptides (Table 1) absorbed onto 3.1 mg per mL of $AlPO_4$ suspension for 1 to 24 hr, were added to 1 mL BAY R1005 stock solution, and the solution mixed gently for 30 minutes at room temperature. The RSV synthetic peptide vaccine formulation was stored at 4° C.

Preparation of PIV3 Vaccine Formulation

A BAY R1005 stock solution of 10 mg/mL was prepared as described above. Ten mL of the desired amount (0.3 to 3 μg per mL) of PIV3 subunit vaccine containing HN and F proteins absorbed onto 3.1 mg per mL of $AlPO_4$ suspension for 1 to 24 hr. The PIV3 subunit vaccine was prepared according to published International patent application WO 91/00104, assigned to the assignee hereof. The alum-absorbed PIV3 antigens were added to 1 mL BAY R1005 stock solution, and the solution mixed gently for 30 minutes at room temperature. The PIV3 vaccine formulation was stored at 4° C.

Preparation of Flu BHA Vaccine Formulation

A BAY R1005 stock solution of 10 mg/mL was prepared as described above. Ten mL of the desired amount (0.5 to 10 μg per mL) of flu BHA subunit vaccine were absorbed onto 3.1 mg per mL of $AlPO_4$ suspension for 1 to 24 hr. The flu BHA subunit vaccine prepared according to Brand and Skehel (Nature New Biol. 1972, 238:145–147), was provided by Dr. D. Burt of Connaught Laboratories Limited, Willowdale, Ont. Canada. The alum-absorbed flu BHA was added to 1 mL BAY R1005 stock solution, and the solution mixed gently for 30 minutes at room temperature. The flu BHA vaccine formulation was stored at 4° C.

Preparation of Pertussis toxoid Vaccine Formulation

A BAY R1005 stock solution of 10 mg/mL was prepared as described above. Ten mL of the desired amount (1 to 20 μg per mL) of pertussis toxoid, prepared according to Tan et al. U.S. Pat. No. 4,997,915, assigned to the assignee hereof, were absorbed onto 3.1 mg per mL of $AlPO_4$ suspension for 1 to 24 hr. The alum-absorbed pertussis toxoid was added to 1 mL of BAY R1005 stock solution, and the solution mixed gently for 30 minutes at room temperature. The pertussis toxoid vaccine formulation was stored at 4° C.

Example 5

This Example describes the general immunization protocol used for testing adjuvant compositions and immunogenic compositions.

Guinea Pig Immunizations

Three guinea pigs were used. The animals were pre-bled at day 0 and then injected IM with 500 μL of the formulation containing the desired amount of antigen, 1.5 mg of $AlPO_4$, and 500 μg of immunodulators BAY R1005 or its derivatives on day 1, 14 and 29. Blood samples were obtained on day 28, and animals were bled out on day 42. The antibody titres were assayed for peptide-specific IgG antibodies using an antigen specific enzyme-linked immunosorbent assay (ELISA). The functional antibody responses were measured using virus neutralization and/or haemagglutination inhibition (HAI) assays and, for pertussis toxoid, the ability of antisera to inhibit induced CHO cell clustering was determined.

Mouse Immunizations

Three to five mice were used. The animals were pre-bled at day 0 and then injected IP with 200 μL of the formulatiion containing the desired amount of antigen, 0.6 mg of $AlPO_4$, and 200 μg of adjuvant BAY R1005 or its derivatives on day 1, 14 and 29. Blood samples were obtained on day 28, and animals were bled out on day 42. The antibody titres were assayed for peptide-specific IgG antibodies using an antigen specific enzyme-linked immunosorbent assay (ELISA). The functional antibody responses were measured using virus neutralization and/or haemagglutination inhibition (HAI) assays.

Example 6

This Example describes an analysis of the immune response to immunogenic compositions.

Antigen-specific ELISAs

Microtiter wells (Nunc-Immunoplate, Nunc, Denmark) were coated with 200 ng of purified antigen (PT, HA, PIV3, HN and F) or 500 ng of individual peptides in 50 μL of coating buffer (15 mM $Na_2CO_3$, 35 mM $NaHCO_3$, pH 9.6) for 16 hr at room temperature. The plates were then blocked with 0.1% (w/v) BSA in phosphate buffer saline (PBS) for 30 minutes at room temperature. Serially diluted antisera were added to the wells and incubated for 1 hr at room temperature. After removal of the antisera, the plates were washed five times with PBS containing 0.1% (w/v) Tween-20 and 0.1 (w/v) BSA. F(ab')$_2$ fragments from goat anti-rabbit, guinea pig, mouse, or human IgG antibodies conjugated to horseradish peroxidase (Jackson ImmunoResearch Labs Inc., Pa.) were diluted (1/8,000) with washing buffer, and added onto the microtiter plates. After 1 hr incubation at room temperature, the plates were washed five times with the washing buffer. The plates were then developed using the substrate tetramethylbenzidine (TMB) in $H_2O_2$ (ADI, Toronto). The reaction was stopped with 1N $H_2SO_4$ and the optical density was measured at 450 nm using a Titretek Multiskan II (Flow Labs., Virginia). Two irrelevant pertussis toxin peptides NAD-S1 (19 residues) and S3(123–154) (32 residues) were included as negative controls in the peptide-specific ELISAs. Assays were performed in triplicate, and the reactive titer of each antiserum was defined as the dilution consistently showing 2-fold increase absorbance value over those obtained from the negative controls.

Haemagglutination Inhibition (HAI) Assays

The assay is based on the capacity of antisera capable of neutralizing either influenza virus or PIV3 to agglutinate red blood cells of guinea pigs (PIV3) or chicken (flu virus). Red blood cells are added to the wells of a 96-well microtitration plate containing serial dilutions of antisera and a constant amount of virus. Following incubation, HAI titer is read by determining the degree of haemagglutinin inhibition. The lowest dilution of antisera blocking haemagglutination is the endpoint titer. A reference sample with a known HAI is run in parallel.

Virus Neutralization Assays

The assay is based on the capacity of antisera to inhibit PIV3 growth in Vero cells. To Vero cells grown on wells of a 96-well microtitration plate, serial dilutions of antisera and a constant amount of virus are added. Following incubation, VN titer of each antisera is read by the determination of 50% inhibition of cytopathic effect caused by PIV3. The lowest dilution of antisera blocking the virus cytopathic effect is the endpoint titer. A reference sample with a known VN titer is run in parallel.

HIV-1 Virus Neutralization Assays

The ability of antisera to neutralize HIV-1 was determined in a syncytia (multi-nuclei giant cells) inhibition assay. Ten $\mu$L of serially diluted antiserum was added to the wells of a 96-well tissue culture plate. 5–10×103 HIV-1 infected CEM cells (in 50 $\mu$L) were then added to each well. $7\times10^4$ uninfected MOLT-4 cells (in 50 $\mu$L) were then added to each well. The plates were then incubated in a $CO_2$ incubator overnight. In samples where no syncytia were formed (i.e. functional, virus-neutralizing antibodies were present in the antiserum), these plates were incubated for a further 24 hours and then reexamined for syncytia formation. The number of syncytia was then scored under an inverted microscope. The lowest dilution of antiserum blocking 90% of virus syncytia formation is the endpoint titer. A reference sample with a known virus neutralizing titer was run in parallel.

Example 7

This Example describes the protocol that can be used for the generation of antigen-specific T-cell lines by immunogenic preparations of the present invention.

BALB/c ($H-2^d$) mice purchased from Charles River Animal Farm (Montreal, Canada) are individually primed subcutaneously with desired amount of amount of antigen (1 to 100 $\mu$g) emulsified with either BAY R1005 or its derivatives. The animals are boosted twice with the same dose of immunogen at 3 week intervals. Ten days after the last boost, spleens of immunized mice are removed. Splenocytes are cultured at $6\times10^5$ cells per well in a final volume of 200 $\mu$L of RPMI 1640 medium (Flow Lab.) supplemented with 10% heat-inactivated fetal calf serum (Gibco), 2 mM L-glutamine (Flow Lab.), 100 U/mL penicillin (Flow Lab.) and $5\times10^{-5}$ M 2-mercaptoethanol (Sigma) in the presence of varying concentrations (1, 10 and 100 $\mu$g per mL) of antigen in 96-well plates (Nunc, Denmark). Cultures are kept in a humidified incubator in the presence of 5% $CO_2$/air. Triplicate cultures are performed for each concentration of antigen. Five days later, 150 $\mu$L of 10% rat concanavalin A culture supernatant diluted in culture medium is added to the microtiter plate wells as a source of Interleukin-2 (IL-2) to expand antigen-specific T-cells. Six days later, 150 $\mu$L of supernatant is removed from each microculture, and 150 $\mu$L of fresh IL-2 containing culture supernatant added to further expand and maintain the viability of the antigen-specific T-cells. After a further 6 day-incubation, the cells are washed three times, each time with 200 $\mu$L of culture medium.

Each set of cultures is then stimulated with the corresponding concentrations (1, 10 and 100 $\mu$g per mL) of the antigen in the presence of $2\times10^5$ irradiated (1,500 rad) BALB/c spleen cells in a final volume of 200 $\mu$L of culture medium. Sixty $\mu$L of supernatant are then removed from each microculture. The supernatants from each triplicate cultures set are pooled. All supernatants are assayed for IL-2, Interleukin-4 and Interferon-gamma (IFN-$\gamma$), using murine IL-2 and IL-4 ELISA kits purchased from Endogen Inc. (MA, USA) respectively. Assay of IFN-$\gamma$ can be done using a mouse IFN-$\gamma$ ELISA kit supplied by Genzyme Corporation (MA, USA). Test culture supernatants can be assayed at 1 in 5 dilution according to the manufacturers' instructions.

Example 8

This Example describes the covalent linkage of BAY R1005 to a peptide.

N-(glutarylacylamido-2-deoxy-$\beta$-D-glucopyranasyl)-N-alkyl-carboxamide which can be used to covalently link BAY R1005 derivatives to either a peptide or protein was synthesized as follows. To a solution of N-(2-amino-2-deoxy-$\beta$-D-glucopyranosyl)-N-alkyl-carboxamide (2 mmol) in dioxane (28 mL) was added di-isopropylethyl amine (8 mmol) and glutaric anhydride (12 mmol). The reaction mixture was stirred overnight at room temperature under argon. Ammonium hydroxide (28 mL) was added to the mixture, and then it was stirred for an additional 18 hours. The product was formed as a precipitate which was filtered, and then redissolved in a solution containing water and t-butanol (2:1). The solution was then acidified by the gradual addition of acetic acid (4 mL). The solution was then lypholized to afford the product in 73% yield, mass spectroscopic analyses (FAB-HRMS) of N-(glutarylacylamido-2-deoxy-$\beta$-D-glucopyranosyl)-N-alkyl-carboxamide, $C_{43}H_{83}N_2O_8$, calculated 755.6149; and found 755.6129.

Resin-bound side-chain protected CLTB-36 peptide was synthesized using F-moc chemistry as follows. Two hundred to 500 mg of resin carrying the N-Fmoc protected first amino acid residue was placed in a reaction vessel. The resin was washed 4 times with DMF, then prewashed with a 50% solution of piperidine in DMF (5 mL for 1 minute) and deprotected with a 50% solution of piperidine in DMF (10 mL for 9 minutes). The resin was then washed with DMF (5 times, 10 mL each). The peptide resin was then coupled with 5 equivalent of the desired Fmoc-protected amino acids activated with phosphonium hexafluorophosphate ester (pfpe) in the presence of DIEA at room temperature for 2 to 3 hr and washed with DMF (5 times, 10 mL each). After the final DMF washing step, an aliquot was taken for a ninhydrine test. If the test was negative, one goes to step 1 for coupling of the next amino acid. If the test was positive or slightly positive, the coupling and DMF washing steps were repeated.

The N-(glutarylacylamido-2-deoxy-$\beta$-D-glucopyranosyl)-N-alkyl-carboxamide was conjugated to synthetic peptide CLTB-36 as follows: N-Hydroxysuccinimide (335 ug, 1.12 eq.) was added to a solution containing the glycolipid prepared as described above (2.0 mg) and dicyclohexylcarbodiimide dissolved in dichloromethane (2 mL). The resulting mixture was then stirred for 4 hours at room temperature. The dicyclohexylurea was filtered and the resulting filtrate was evaporated to dryness. The dried active ester was redissolved in DMF (0.1 mL) and was added into a peptide-resin containing side-chain protected CLTB-36 at molar ratio of 1.1 to 1. The reaction mixture was stirred overnight at room temperature. The excess reagents were filtered and the peptide-resin was washed with 4×10 mL of dichloromethane. After drying, the peptide-resin was treated with TFA to release lipidated CLTB-36 from resin. The crude lipidated peptide was further purified by HPLC using a C4 Vydac column (1×35 cm) with a acetonitrile gradient from 20 to 60% developed within 40 minutes at a flow rate 2 mL/minute. Amino acid composition analyses of lipidated CLTB-36 performed on a Waters Pico-Tag system were in good agreement with their theoretical compositions, and the presence of fatty acids were confirmed by GC analyses of the acid hydrolysate.

The N-(glutarylacylamido-2-deoxy-β-D-glucopyranosyl-N-alkyl-carboxamide was conjugated to flu recombinant NP protein as follows: N-Hydroxysuccinimide (335 ug, 1.12 eq.) was added to a solution containing the glycolipid prepared as described above (2.0 mg) and dicyclohexylcarbodiamide dissolved in dichloromethane (2 mL). The resulting mixture was then stirred for 4 hours at room temperature. The dicyclohexylurea was filtered and the resulting filtrate was evaporated to dryness. The dried active ester (2.25 mg) was redissolved in DMF (0.1 mL) and was added into a protein solution (2 mg rNP1 protein dissolved in 2 mL of 25 mM phosphate buffer, pH 7.8) at a molar ratio of 20:1. The reaction mixture was stirred overnight at 4° C., and then was dialysed against 4×4 L of the phosphate buffer. The incorporation of N-(glutarylacylamido-2-deoxy-B-D-glucopyranosyl)-N-alkyl-carboxamide to flu recombinant NP was determined and confirmed using gas chromatography (GC) for lipid analyses of the acid hydrolysate (6 N of HCI for 2 hr at 110° C.) of the modified protein.

The present invention has been exemplified by reference to particular examples and embodiments. Numerous adaptations, variations and modifications may be made to the particular examples and embodiments without departing from the essence of the invention which is defined in the claims.

SUMMARY OF THE DISCLOSURE

In summary of this disclosure, the present invention provides novel adjuvant compositions which are able to elicit an enhanced immune response against antigens and novel compounds comprising antigen covalently bonded to a glycolipid analog. Modifications are possible within the scope of the invention.

TABLE 1

SYNTHETIC PEPTIDES USED IN THE STUDIES

| PEPTIDES | AMINO ACID SEQUENCE | SEQ ID NO: |
|---|---|---|
| HIV peptides | | |
| CLTB-36 | GPKEPFRDYVDRFYKNRKRIHIGPGRAFYTTKN | 1 |
| CLTB-70 | GPKEPFRDYVDRFYKNTRKSIYIGPGAFHTTGR | 2 |
| CLTB-72 | GPKEPFRDYVDRFYKNTRKRIRIQRGGRAFVTIGK | 3 |
| CLTB-74 | GPKEPFRDYVDRFYKNTRKSITKGPGRVIYATGQ | 4 |
| CLTB-76 | GPKEPFRDYVDRFYKNTRQSTPIGLGQALYTTRG | 5 |
| P24E-GP41C | GPKEPFRDYVDRFYKSLIEESQNQQEKNEQELLELDKWAS | 6 |
| RSV peptides | | |
| RSV-F | QSYSIMSIIKEEVLAYAVQLPLPLYGVIDTP | 7 |
| RSV-FND2 | PIVNKQSCSISNIETVIEFQQ | 8 |
| RSV-G1 | TKQRQNKPPSKPNNDFHFEVFNFVPC | 9 |
| RSV-G2 | CSNNPTCWAICKRIPNKKPGKKT | 10 |
| pertussis peptide | | |
| 69K-P1 | PQPGPQPPQPPQPQPEAPAPQPPC | 11 |
| Hib peptides | | |
| HIBP1-5E | NQITSALSTQQEFRDLKKYLPSKDKSVVSLQDRAC | 12 |
| TBP2-3 | TVGKKTYQVEACCSNLSYVKFGM | 13 |
| Rubella virus peptide | | |
| RV-EP2 7 | PDPGDLVEYIMNYTGNQQSRWGLGSPNCHGPDWASPVCQRHSP | 14 |
| *S. pneumoniae* peptide | | |
| PSP-AA | IKEIDESESEDYAKEGFRAP | 15 |

TABLE 2

Guinea pigs antibody responses to synthetic peptides formulated with different adjuvants

| Peptide Immunogens[2] | Peptide-Specific Antibody Titre[1] Adjuvants used in the immunization PBS | CFA | alum | BAY R1005 | TPC | OTH |
|---|---|---|---|---|---|---|
| CLTB-36 | 400 | 256,000 | 10,000 | 72,800 | 3,200 | 6,400 |
| CLTB-70 | 2,500 | 312,500 | 116,666 | 133,333 | 6,400 | 12,800 |
| CLTB-72 | 2,333 | 312,500 | 37,500 | 45,800 | 3,200 | 6,400 |
| CLTB-74 | 2,500 | 625,000 | 43,055 | 212,500 | 6,400 | 25,600 |
| CLTB-76 | 1,833 | 625,000 | 9,166 | 45,833 | 3,200 | 6,400 |
| P24E-GP41C | 2,500 | 625,000 | 29,166 | 45,833 | 12,800 | 12,800 |
| RSV-F | 500 | 6,400 | 32,000 | 3,850 | 1,600 | 3,200 |
| RSV-FND2 | 400 | 12,800 | 7,800 | 10,000 | 3,200 | 6,400 |
| RSV-G2 | 1,280 | 128,000 | 31,500 | 3,200 | 1,600 | ND[3] |
| RSV-G1 | 1,600 | 315,000 | 128,000 | 31,500 | 6,400 | ND |
| RV-EP27 | 400 | 128,000 | 12,800 | 800 | 6,400 | 25,600 |
| HIBP1-5E | 200 | 312,500 | 8,333 | 32,500 | 1,600 | ND |
| 69K-P1 | 800 | 10,000 | 32,500 | 32,500 | 1,600 | ND |

TABLE 2-continued

Guinea pigs antibody responses to synthetic peptides formulated with different adjuvants

| | Peptide-Specific Antibody Titre[1] Adjuvants used in the immunization | | | | | |
|---|---|---|---|---|---|---|
| Peptide Immunogens[2] | PBS | CFA | alum | BAY R1005 | TPC | OTH |
| TBP2-3 | 400 | 12,500 | 43,333 | 32,500 | ND | ND |
| PSP-AA | 200 | 12,500 | 1,600 | 400 | ND | ND |

[1]Mean titer of three guinea pigs received three injections.
[2]All peptide immunogen except CLTB-36 are used 100 µg of peptide per dose formulated with different adjuvants. CLTB-36 is used 20 µg of peptide per dose.
[3]Not done.

TABLE 3

Guinea pigs antibody responses to synthetic peptides formulated with different adjuvants

| | Peptide-Specific Antibody Titre[1] Adjuvants used in the immunization | | |
|---|---|---|---|
| Peptide Immunogens[2] | alum | BAY R1005 | BAY R1005 + alum |
| RSV-F | 32,000 | 3,850 | 128,000 |
| RSV-FND2 | 7,800 | 10,000 | 25,600 |
| RV-EP27 | 12,800 | 800 | 64,000 |

[1]Mean titer of three guinea pigs received three injections.
[2]All peptide immunogens are used 100 µg of peptide per dose formulated with different adjuvants.

TABLE 4

ANTIBODY RESPONSE TO CLTB-36 FORMULATED IN DIFFERENT ADJUVANTS

| | | Average titers against | | |
|---|---|---|---|---|
| Antisera[1] | Dose (20 µg) | CLTB-36 | CLTB-56[2] | Virus Syncytia-formation |
| Guinea pigs | alum | 6,400 | 1,833 | <10 |
| | BAY R1005 | 62,500 | 4,333 | 15 |
| | alum + BAY R1005 | 36,500 | 6,250 | 24 |
| | BAY R1005 conjugated | 20,833 | 5,833 | 23 |
| | 100 µg in alum[3] | 32,000 | 12,500 | 32 |

[1]Groups of guinea pigs (n = 3) were immunized with 20 µg of CLTB-36 emulsified in BAY R1005 and/or absorbed onto alum at day 1. Booster immunizations were at 2, 4 and 6 weeks with the same antigens. Blood samples were collected every 2 weeks after the third injection. Sera were analyzed by peptide-specific ELISAs, virus neutralization and syncytia formation inhibition assays.

[2]Peptide CLTB-56 is the B-cell epitope of CLTB-36 and has amino acid sequence of NKRKRIHIGPGRAFYTTKN (SEQ ID NO: 16).

[3]A 100 µg of CLTB-36 absorbed onto alum was used.

What we claim is:

1. An adjuvant composition for modulating an immune response to an antigen administered to a host, the composition consisting essentially of:
   (a) a mineral salt adjuvant which is selected from the group consisting of aluminum hydroxide, aluminum phosphate, calcium phosphate, zinc hydroxide and calcium hydroxide; in admixture with
   (b) at least one other adjuvant selected from the group consisting of (A) a glycosylamide which is a glycosylamide having the formula:

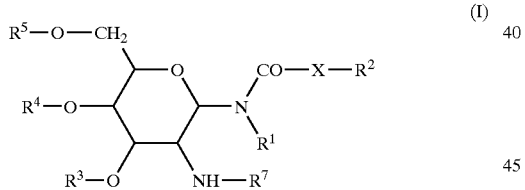

(I)

in which
   R1 denotes hydrogen or saturated or singly or multiply unsaturated alkyl radical having up to 50 carbon atoms;
   X represents —CH$_2$—, —O— or —NH—,
   R2 denotes hydrogen or saturated or singly or multiply unsaturated alkyl radical having up to 50 carbon atoms;
   R3, R4, and R5, independently of one another, denotes hydrogen, or SO$_4^{2-}$, or PO$_4^{2-}$, or other negatively charged moiety, or —CO—R6, R6 being an alkyl radical having up to 10 carbon atoms;
   R7 is L-alanyl, L-alpha-amino butyryl, L-arginyl, L-asparginyl, L-aspartyl, L-cysteinyl, L-glutamyl, L-glycyl, L-histidyl, L-hydroxypropyl, L-isoleucyl, L-leucyl, L-lysyl, L-methionyl, L-omithinyl, L-phenylalanyl, L-prolyl, L-seryl, L-threonyl, L-tyrosyl, L-tryptophanyl, and L-valyl or their D-isomers; and pharmaceutically acceptable salts of said gycosylamide, (B) an octadecyl ester of an aromatic amino acid and (C) a lipopeptide which is tripalmityl-S-glyceryl-cysteinylserylserine or N-palmityl-S-[2,3-(bis(palmityloxy))-2-(RS)propyl-[R]-cysteine.

2. The composition of claim 1, wherein the aromatic amino acid is tyrosine.

3. An immunogenic composition for eliciting an immune response in a host, the composition consisting essentially of an admixture of:
   (a) at least one antigen;
   (b) a mineral salt adjuvant which is selected from the group consisting of aluminum hydroxide, aluminum phosphate, calcium phosphate, zinc hydroxide and calcium hydroxide; and
   (c) at least one other adjuvant selected from the group consisting of (A) a glycosylamide which is a glycosylamide having the formula:

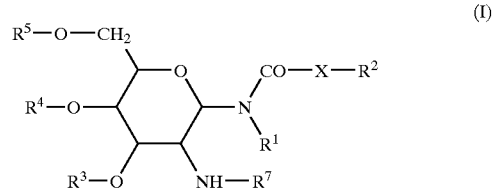

(I)

in which
   R1 denotes hydrogen or saturated or singly or multiply unsaturated alkyl radical having up to 50 carbon atoms;
   X represents —CH$_2$—, —O— or —NH—,
   R2 denotes hydrogen or saturated or singly or multiply unsaturated alkyl radical having up to 50 carbon atoms;
   R3, R4, and R5, independently of one another, denotes hydrogen, or SO$_4^{2-}$, or PO$_4^{2-}$, or other negatively charged moiety, or —CO—R6, R6 being an alkyl radical having up to 10 carbon atoms;
   R7 is L-alanyl, L-alpha-amino butyryl, L-arginyl, L-asparginyl, L-aspartyl, L-cysteinyl, L-glutamyl, L-glycyl, L-histidyl, L-hydroxypropyl, L-isoleucyl, L-leucyl, L-lysyl, L-methionyl, L-ornithinyl, L-phenylalanyl, L-prolyl, L-seryl, L-threonyl, L-tyrosyl, L-tryptophanyl, and L-valyl or their D-isomers; and pharmaceutically acceptable salts of said clycosylamide, (B) an octadecyl ester of an aromatic amino acid and (C) a lipopeptide which is tripalmityl-S-glyceryl-cysteinylserylserine or N-palmityl-S-[2,3-(bis(palmityloxy))-2-(RS)propyl-[R]-cysteine.

4. The composition of claim 3, wherein the aromatic amino acid is tyrosine.

5. An immunogenic composition for eliciting an immune response in a host, the composition consisting essentially of an admixture of:
  (a) at least one antigen;
  (b) a mineral salt adjuvant which is selected from the group consisting of aluminum hydroxide and aluminum phosphate; and
  (c) a the glycosylamide which is N-(2-deoxy-2-L-leucylamino-β-D-glucopyranosyl)-N-octadecyidodecanamide acetate.

6. The composition of claim 5 wherein said mineral salt adjuvant is aluminum phosphate.

7. The composition of claim 5 wherein the antigen is selected from the group consisting of microbial pathogens, bacteria, viruses, proteins, glycoproteins, lipoproteins, peptides, glycopeptides, lipopeptides, toxoids, carbohydrates and tumor-specific antigens.

8. The composition of claim 7, wherein the antigen comprises a protein, glycoprotein or lipoprotein, or a peptide, glycopeptide or lipopeptide which includes an amino acid sequence corresponding to an antigenic determinant of an HIV, Rubella virus, Respiratory Syncytial Virus, influenza virus, *Bordetella pertussis, Haemophilus influenzae* or *Streptococcus pneumoniae*.

9. The composition of claim 8, wherein the peptide includes an amino acid sequence shown in Table 1.

10. The composition of claim 7, wherein the antigen comprises a toxoid which is pertussis toxoid.

11. The composition of claim 7, wherein the protein is influenza haemagglutinin or a human parainfluenza virus subunit.

12. A method of modulating an immune response to an antigen comprising combining an antigen with the adjuvant composition of claim 1.

13. A method of generating an immune response in a host comprising administering thereto the composition of claim 5.

14. The method of claim 13, wherein the immune response is a humoral or a cell-mediated immune response.

15. A kit for preparing an immunogenic composition, consisting essentially of:
  (a) container means containing a mineral salt adjuvant which is selected from the group consisting of aluminum hydroxide and aluminum phosphate;
  (b) container means containing a glycosylamide which is N-(2-deoxy-2-L-leucylamino-β-D-glucopyranosyl)-N-octadecyldodecanamide acetate;
  (c) container means containing at least one antigen; and
  (d) mixer means for combining the mineral salt adjuvant, the glycosylamide and at least one antigen into an admixture to produce the immunogenic composition.

* * * * *